(12) United States Patent
Li et al.

(10) Patent No.: US 7,338,663 B2
(45) Date of Patent: Mar. 4, 2008

(54) EXPANDABLE OSMOTIC COMPOSITION AND COATING SUSPENSION

(75) Inventors: Shaoling Li, Sunnyvale, CA (US); Liang-Chang Dong, Sunnyvale, CA (US); Padmaja Shivanand, Los Altos, CA (US); Patrick S. L. Wong, Burlingame, CA (US)

(73) Assignee: ALZA Corporation, Mountain View, CA (US)

( * ) Notice: Subject to any disclaimer, the term of this patent is extended or adjusted under 35 U.S.C. 154(b) by 555 days.

(21) Appl. No.: 10/609,061

(22) Filed: Jun. 28, 2003

(65) Prior Publication Data

US 2004/0058002 A1 Mar. 25, 2004

Related U.S. Application Data

(60) Provisional application No. 60/392,775, filed on Jun. 28, 2002.

(51) Int. Cl.
*A61K 9/00* (2006.01)
(52) U.S. Cl. ............... 424/400; 514/772; 514/772.1
(58) Field of Classification Search ............. None
See application file for complete search history.

(56) References Cited

U.S. PATENT DOCUMENTS

| | | | |
|---|---|---|---|
| 4,765,989 A | 8/1988 | Wong et al. | |
| 5,324,280 A | 6/1994 | Wong et al. | |
| 5,413,572 A | 5/1995 | Wong et al. | |
| 5,531,736 A | 7/1996 | Wong et al. | |
| 5,800,422 A * | 9/1998 | Dong et al. | 604/892.1 |
| 6,352,721 B1 | 3/2002 | Faour | |
| 6,419,952 B2 * | 7/2002 | Wong et al. | 424/463 |
| 2001/0036472 A1 | 11/2001 | Wong et al. | |

OTHER PUBLICATIONS

"NATROSOL" disclosure, downloaded from the world wide web on Nov. 27, 2006.*

* cited by examiner

*Primary Examiner*—Michael P. Woodward
*Assistant Examiner*—Eric E. Silverman
(74) *Attorney, Agent, or Firm*—Angela N. Nwaneri

(57) ABSTRACT

The present invention includes an expandable osmotic layer and a coating suspension for providing an expandable osmotic layer, both of which are useful for the manufacture of controlled release dosage forms. The expandable osmotic layer of the present invention may be produced using the coating suspension of the present invention. Advantageously, the coating suspension of the present invention can be used to coat expandable osmotic layers under both wet and dry process conditions without sacrificing the quality of the expandable osmotic layers produced, and therefore provides a relatively robust coating suspension that facilitates commercial production of controlled release dosage forms including a coated expandable osmotic layer.

44 Claims, 3 Drawing Sheets

TABLE 1

| Coating Run | Formulation | Inlet Temp (C) | Outlet Temp (C) | Spray Rate (g/min/gun) | Pan Speed (RPM) | Pan Air Vol (CFM) | Pan Exhaust Pressure | Gun-to-Bed Distance (inch) | Atomization Air Vol (SLPM) | Pattern Air Vol (SLPM) | Efficiency (%) | |
|---|---|---|---|---|---|---|---|---|---|---|---|---|
| 24-12 | 1 | 52-54 | 35-36 | 45 | 10 | 300-330 | -1 | 5 | 100 | 40 | 71 | DRY |
| 24-13 | 1 | 52-53 | 32-34 | 50 | 10 | 320-330 | -1 | 5 | 100 | 40 | 82 | WET |
| 24-14 | 2 | 52-54 | 34-36 | 45 | 10 | 340-350 | -1 | 5 | 100 | 40 | 87 | WET |
| 24-15 | 2 | 53-55 | 35-37 | 40 | 10 | 340-350 | -1 | 5 | 100 | 40 | 78 | DRY |
| 24-16 | 3 | 53-54 | 33-34 | 45 | 10 | 310-320 | -1 | 5 | 100 | 40 | 80 | DRY |
| 24-17 | 3 | 51-52 | 32-35 | 50 | 10 | 330-350 | -1 | 5 | 100 | 40 | 90 | WET |
| 24-18 | 4 | 52-53 | 34-35 | 45 | 10 | 340-345 | -1 | 5 | 100 | 40 | 89 | WET |
| 24-19 | 4 | 52-54 | 36-37 | 40 | 10 | 340-350 | -1 | 5 | 100 | 40 | 81 | DRY |

FIG. 4

TABLE 2

| Coating Run | Formulation | | | | | Coating Condition | % Coating Efficiency (Osmotic Coating) | % System Cracked | |
|---|---|---|---|---|---|---|---|---|---|
| | NaCMC(%) | Natrosol(%) | NaCl(%) | Water(%) | Ethanol(%) | | | Osmotic Coated | CA Membrane Coated |
| 24_12 | 4.9 | 3 | 8.1 | 62.7 | 21.3 | DRY | 71 | 0.00 | 0.00 |
| 24_13 | 4.9 | 3 | 8.1 | 62.7 | 21.3 | WET | 82 | 0.19 | 1.98 |
| 24_14 | 4.1 | 5 | 6.9 | 62.7 | 21.3 | WET | 87 | 0.00 | 0.00 |
| 24_15 | 4.1 | 5 | 6.9 | 62.7 | 21.3 | DRY | 78 | 0.00 | 0.12 |
| 24_16 | 4.9 | 3 | 8.1 | 65.3 | 18.7 | DRY | 80 | 0.00 | 0.00 |
| 24_17 | 4.9 | 6 | 8.1 | 65.3 | 18.7 | WET | 90 | 0.14 | 4.95 |
| 24_18 | 4.1 | 5 | 6.9 | 65.3 | 18.7 | WET | 89 | 0.00 | 0.00 |
| 24_19 | 4.1 | 5 | 8.9 | 65.3 | 18.7 | DRY | 81 | 0.00 | 0.00 |

FIG. 5

EXPANDABLE OSMOTIC COMPOSITION AND COATING SUSPENSION

This application claims the benefit of U.S. Provisional Application No. 60/392,775, filed Jun. 28, 2002.

BACKGROUND

1. Field of the Invention:

The present invention relates to controlled release dosage forms. Specifically, the present invention provides an improved expandable osmotic layer and an improved expandable osmotic layer coating suspension, both of which better facilitate commercial manufacture of controlled release dosage forms utilizing a coated, expandable osmotic layer.

2. State of the Art:

Controlled release dosage forms created using a coated, expandable osmotic layer are known in the art. For example, U.S. Pat. No. 5,413,572 ("the '572 Patent"), U.S. Pat. No. 5,324,280 ("the '280 Patent") and U.S. application Ser. No. 09/866,036 ("the '036 Application"), now U.S. Pat. No. 6,419,952, all teach controlled release dosage forms created by coating hard or soft gelatin capsules with an expandable osmotic layer. In general, the controlled release liquid capsules taught in these publications include a capsule that is pre-filled with a liquid active agent formulation, an expandable osmotic layer formed around the pre-filled capsule, a semipermeable layer formed around the expandable osmotic layer, and an exit orifice through which the liquid active agent formulation included in the capsule is delivered as the dosage form operates. As taught in the '036 Application, a baffler layer may be positioned between the capsule and the expandable osmotic layer in order to achieve more consistent and better controlled delivery of the liquid active agent formulation.

In use, the controlled release dosage forms taught in the '572 Patent, the '280 Patent, and the '036 Application draw water from their environment of use through the semipermeable layer and into the expandable osmotic layer. As water is absorbed into the expandable osmotic layer, the expandable osmotic layer expands and compresses the capsule such that the liquid formulation contained therein is expelled through the exit orifice at a controlled rate over a desired period of time. Although the controlled release dosage forms taught in the referenced publications achieve the controlled release of active agent formulations, it has been found that the formulation of the expandable osmotic layer included in these dosage forms creates some difficultly when attempting to produce such dosage forms at a commercial scale. In particular, the expandable osmotic layer formulation taught in the '572 Patent, the '280 Patent, and the '036 Application has proven to be sensitive to processing conditions, exhibiting a tendency to produce cracked osmotic layers if the process conditions are not closely monitored to provide dry process conditions.

The expandable osmotic layer of the controlled release liquid capsules taught in the referenced publications typically includes an osmopolymer, such as sodium carboxy methylcellulose (NaCMC), an osmotic agent, such a NaCl, and a film former, such as hydroxyethylcellulose (NATRASOL®) To coat an intermediate dosage form with an expandable osmotic layer incorporating these constituents, a coating suspension suitable for a spray coating process is typically formulated by mixing the solid constituents included in the expandable osmotic layer into a two solvent system, such as a water and ethanol solvent mixture. Once the coating suspension is formed, the expandable osmotic layer is coated on intermediate dosage forms using, for example, a known spray coating technique. As is well known, spray coating processes generally involve agitating a batch of devices to be coated (in this case, a batch of intermediate dosage forms) while spraying a coating formulation over or around the devices such that, over a period of time, the devices are coated with a material layer of desired thickness. Coating suspensions previously used to coat an expandable osmotic layer included 4.9 wt % NaCMC, 8.1 wt % NaCl, 3.0 wt % NATRASOL®, and 84 wt % solvent mixture, such as, for example a mixture of 62.7 wt % water and 21.3 wt % EtOH solvent. The previously used coating suspensions typically produced expandable osmotic coatings including 30.6 wt % NaCMC, 50.6 wt % NaCl, and 18.8 wt % NATRASOL®. Although coating suspensions according to the previous formulations generally produce osmotic layers of acceptable quality when the spray coating conditions are closely monitored to ensure a dry coating process, under wet processing conditions, such coating suspensions produce an unacceptably high number of coated devices having expandable osmotic layers tat are cracked and, therefore, unsuitable for further processing.

The process sensitivity of the previous coating suspensions and resulting expandable osmotic layers are disadvantageous from at least two standpoints. First, as dosage forms are processed at a commercial scale, it becomes more difficult to precisely control process parameters. Therefore, a coating suspension that provides acceptable material only under particular process conditions is undesirable, because, at a commercial scale, the quality of the material layers produced using such a coating suspension may be unpredictable. Second, wet spray coating processes (i.e., spray coating processes characterized by relatively higher solvent concentrations in the coating environment) are generally recognized as more efficient. Yet in order to produce expandable osmotic layers of a desired level of quality and performance, the previous coating suspensions require that the expandable osmotic layers be coated under dry process conditions. As is easily understood, such a requirement is particularly disadvantageous in a commercial context because it forces the use of a less efficient process and leads to increases in the required process times, the amounts of materials used, and, ultimately, the cost of manufacturing the dosage form.

In order to avoid the potential disadvantages exhibited by the previous coating suspensions and the expandable osmotic layers produced thereby, it would be desirable to provide a coating suspension that is less process sensitive. In doing so, however, the function of the expandable osmotic layer must be considered and preserved. Both the osmotic activity and the expansion capabilities of an expandable osmotic layer included in a controlled release dosage form are essential to the proper function of the device. It would be an improvement in the art, therefore, to provide an expandable osmotic layer and coating suspension that are less sensitive to process conditions, yet do not compromise the function of a controlled release dosage form. Such an expandable osmotic layer and coating suspension would not only allow the coating of the expandable osmotic layer under varying process conditions but would facilitate commercial production of controlled release dosage forms including coated expandable osmotic layers.

SUMMARY OF THE INVENTION

The present invention includes a coating suspension for providing an expandable osmotic layer for controlled release dosage forms, such as, for example, a controlled release liquid capsule. Advantageously, the coating suspension of the present invention exhibits less process sensitivity than previously used coating formulations, allowing an expandable osmotic layer to be coated under both wet and dry conditions. Moreover, the osmotic activity and expansion capabilities of the expandable osmotic layers provided by the coating suspension of the present invention allow the fabrication of controlled release dosage forms exhibiting desirable performance characteristics. The coating suspension of the present invention of the present invention, therefore, facilitates commercial production of controlled release dosage forms including a coated expandable osmotic layer, as it provides osmotic layers of consistent quality under varying process conditions and allows the use of more efficient coating processes.

When compared to a dry spray coating process, a wet spray coating process is characterized by a relatively higher solvent concentration in the coating environment. As is well known, adjusting the "dryness" or "wetness" of a particular spray coating process can be accomplished by altering one or more of several process parameters, such as, for example, inlet temperature, spray rate, agitation speed, air volume, exhaust pressure, and gun-to-bed distance. However, a set of process parameters producing a wet process for a particular coating application will not necessarily produce a wet process for a different coating application. In fact, the process parameters necessary to achieve a wet or dry coating process typically change as the coating formulation or the material being coated changes. Because wet processes are generally recognized as providing more efficient spray coating, however, wet and dry spray coating processes may be defined by the coating efficiencies achieved. As the expressions "dry spray coating process" and "dry processing conditions" are used in relation to the coating suspension or expandable osmotic layer of the present invention, such expressions indicate process conditions that result in a coating efficiency of about 80% or less, while the expressions "wet spray coating process" and "wet process conditions" are used in relation to the coating suspension or expandable osmotic layer of the present invention to indicate process conditions that result in a coating efficiency of about 85% or more.

The present invention also provides an expandable osmotic layer, which may be produced by the coating suspension of the present invention. The expandable osmotic layer of the present invention is suitable for use in controlled release dosage forms, such as, for example, controlled release liquid capsules. Significantly, even though the relative percentages of the components making up the expandable osmotic layer of the present invention are substantially changed relative to the expandable osmotic layers previously used, the expandable osmotic layer of the present invention does not compromise the controlled release function of the dosage forms into which it is incorporated.

A controlled release dosage form is also included within the scope of the present invention. The controlled release dosage form of the present invention may be manufactured using the coating suspension of the present invention and incorporates the expandable osmotic layer of the present invention. In one embodiment, the controlled release dosage form of the present invention is a controlled release liquid capsule. The controlled release dosage form of the present invention, however, is not limited to dosage forms incorporating liquid filled capsules, but includes any dosage form incorporating an expandable osmotic layer according to the present invention.

The present invention also includes a method of manufacturing a controlled release dosage form. Generally, the method of the present invention includes providing an intermediate dosage form to be coated with an osmotic layer and coating the intermediate dosage form with an expandable osmotic layer according to the present invention. In specific embodiments, the method of the present invention may additionally include providing a coating suspension of the present invention and coating an expandable osmotic layer according to the present invention using a spray coating process.

Figure 1:
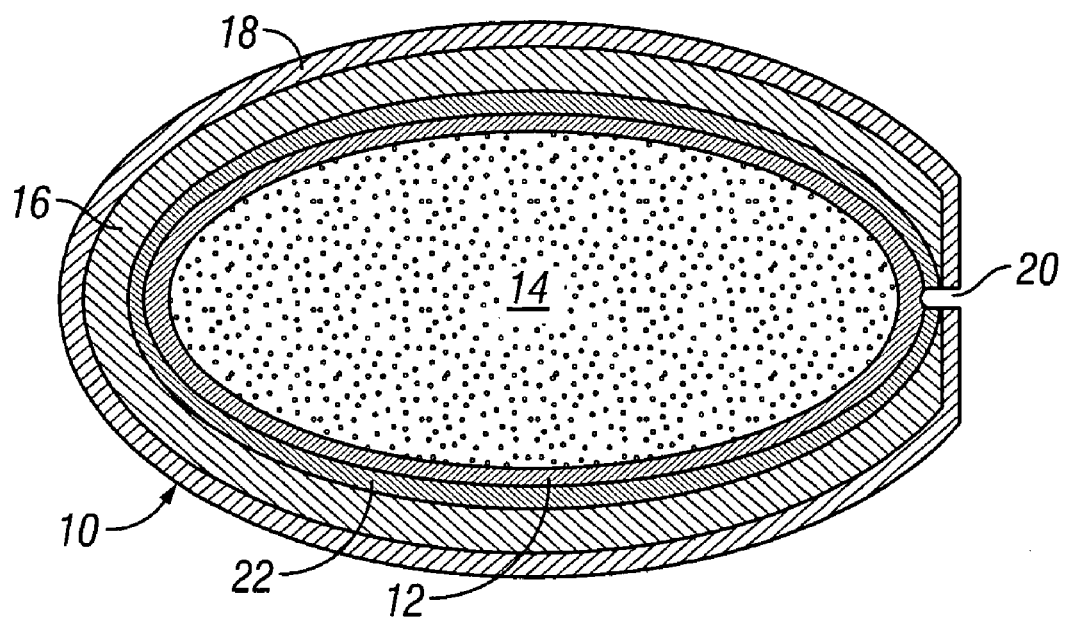
FIG. 1 illustrates an embodiment of the dosage form according to the present invention.

Table 1 details the process conditions used in each of the eight coating runs described in Example 1.

Table 2 details the results achieved in each of the eight coating runs described in Example 1.

DETAILED DESCRIPTION OF THE INVENTION

The coating suspension of the present invention includes an osmopolymer, an osmotic agent, and a film former. The coating suspension of the present invention, however, includes a relatively larger amount of film former and relatively smaller amounts of osmopolymer and osmotic agent, as compared to previous coating suspension formulations. Specifically, the coating formulation of the present invention includes about 5 wt % to about 7 wt % film former is formulated with a solids content of about 16 wt % to about 20 wt %, with a solids content of about 16 wt % to about 18 wt % being preferred. Therefore, the osmopolymer and osmotic agent included in the coating suspension of the present invention account for about 9 wt % to about 15 wt % of the coating suspension, with the osmopolymer and osmotic agent preferably accounting for about 9 wt % to about 13 wt % of the coating suspension. Although the amount of osmopolymer and osmotic agent will vary as the amount of film former included in the coating suspension varies, the ratio of osmopolymer to osmotic agent included in the coating suspension of the present invention is maintained at between about 0.5:1 and about 0.7:1, with the coating suspension being preferably formulated with an osmopolymer to osmotic agent ratio of about 0.6:1.

Given the desired range of solids content, the desired range of film former content, and the desired ratio of osmopolymer to osmotic agent included in a coating suspension of the present invention, various different embodiments of the coating suspension of the present invention can be formulated. As a coating suspension of the present invention includes about 16 wt % to about 20 wt % solids content and the film former accounts for about 5 wt % to about 7 wt %, the osmopolymer included in the coating suspension will typically account for about 3 wt % to about 6.2 wt % of the coating suspension, and the osmotic agent will typically account for about 5.3 wt % to about 10 wt % of the coating suspension.

In one embodiment, the coating suspension of the present invention includes about 5 wt % film former, with a total solids content of about 16 wt %. In such an embodiment, the coating suspension will typically include about 3.7 wt % to about 4.5 wt % osmopolymer and about 6.5 wt % to about 7.3 wt % osmotic agent, with about 4.1 wt % osmopolymer and about 6.9 wt % osmotic agent being preferred.

In another embodiment of a coating suspension of the present invention, the coating suspension includes about 6 wt % film former, with a total solids content of about 16 wt %. In such an embodiment, the coating suspension will typically include about 3.3 wt % to about 4.1 wt % osmopolymer and about 5.9 wt % to about 6.7 wt % osmotic agent, with about 3.7 wt % osmopolymer and about 6.3 wt % osmotic agent being preferred.

In another embodiment of a coating suspension of the present invention, the coating suspension includes about 7 wt % film former, with a total solids content of about 16 wt %. In such an embodiment, the coating suspension will typically include about 3 wt % to about 3.7 wt % osmopolymer and about 5.3 wt % to about 6 wt % osmotic agent, with about 3.4 wt % osmopolymer and about 5.6 wt % osmotic agent being preferred.

In another embodiment of a coating suspension of the present invention, the coating suspension includes about 5 wt % film former, with a total solids content of about 18 wt %. In such an embodiment, the coating suspension will typically include about 4.3 wt % to about 5.4 wt % osmopolymer and about 7.6 wt % to about 8.7 wt % osmotic agent, with about 4.9 wt % osmopolymer and about 8.1 wt % osmotic agent being preferred.

In another embodiment, a coating suspension of the present invention, the coating suspension includes about 6 wt % film former, with a total solids content of about 18 wt %. In such an embodiment, the coating suspension will typically include about 4 wt % to about 4.9 wt % osmopolymer and about 7.1 wt % to about 8 wt % osmotic agent, with about 4.5 wt % osmopolymer and about 7.5 wt % osmotic agent being preferred.

In another embodiment, the coating suspension of the present invention includes about 7 wt % film former, with a total solids content of about 18 wt %. In such an embodiment, the coating suspension will typically include about 3.7 wt % to about 4.5 wt % osmopolymer and about 6.5 wt % to about 7.3 wt % osmotic agent, with about 4.1 wt % osmopolymer and about 6.9 wt % osmotic agent being preferred.

In another embodiment of the coating suspension of the present invention, the coating suspension includes about 5 wt % film former, with a total solids content of about 20 wt %. In such an embodiment, the coating suspension will typically include about 5 wt % to about 6.2 wt % osmopolymer and about 8.8 wt % to about 10 wt % osmotic agent, with about 5.6 wt % osmopolymer and about 9.4 wt % osmotic agent being preferred.

In another embodiment, the coating suspension of the present invention includes about 6 wt % film former, with a total solids content of about 20 wt %. In such and embodiment, the coating suspension of the present invention will typically include about 4.7 wt % to about 5.8 wt % osmopolymer and about 8.2 wt % to about 9.3 wt % osmotic agent, with about 5.3 wt % osmopolymer and about 8.7 wt % osmotic agent being preferred.

In another embodiment, the coating suspension of the present invention includes about 7 wt % film former, with a total solids content of about 20 wt %. In such and embodiment, the coating suspension of the present invention will typically include about 4.3 wt % to about 5.4 wt % osmopolymer and about 7.6 wt % to about 8.7 wt % osmotic agent, with about 4.9 wt % osmopolymer, and about 8.1 wt % osmotic agent being preferred.

The solids included in the coating suspension of the present invention are typically mixed into a two part solvent mixture that is suitable for forming a coating suspension useful in a spray coating process. The two part solvent mixture includes an organic solvent and an aqueous solvent, wherein the organic solvent is miscible with the aqueous solvent. The organic solvent is preferably chosen such that the osmopolymer included in the coating suspension is poorly soluble in the organic solvent. Organic solvents that may be included in a two part solvent mixture of a coating suspension of the present invention include, for example, ethanol, isopropyl alcohol, and acetone. As the solids content of the coating suspension of the present invention increases, the relative amount of organic solvent included in the two part solvent mixture will also increase in order to maintain desirable coating characteristics. The relative amounts of organic solvent and aqueous solvent used in a coating suspension according to the present invention may also vary as the solvents, the osmopolymer, the osmotic agent, and the film former included in the coating suspension vary.

In preferred embodiments of the coating suspension of the present invention, the two part solvent mixture accounts for between about 80 wt % and about 84 wt % of the coating suspension, with a coating suspensions including from about 82 wt % to about 84 wt % of the two part solvent mixture being preferred. Preferred solvents for use in the two part solvent mixture are ethanol and water. Where, the coating suspension of the present invention includes a two part solvent system formed of ethanol and water, the ratio of ethanol to water preferably ranges from about 1:2 to about 1:4, with a range of about 1:2.2 to about 1:3.5 being most preferred. For example, where the coating suspension of the present invention includes 16 wt % solids, the ratio of ethanol to water preferably ranges from about 1:3 to about 1:3.5. However, where the coating suspension of the present invention includes 20 wt % solids, the coating suspension is preferably formulated to have an ethanol to water ratio of about 1:2 to about 1:2.2.

In preferred embodiments of the coating suspension of the present invention, the film former is NATRASOL®, the osmopolymer is NaCMC, and the osmotic agent is NaCl. However, the coating suspension of the present invention, is not limited to the use of such materials. For example, the film former included in the coating suspension of the present invention may also be selected from, for example, hydroxypropyl methylcellutose ("HPMC"), methylcellulose ("MC"), polyvinylalcohol-polyethylene glycol graft polymer (Kollicoat® IR), and polyvinyl-pyrrolidone polymers, such as KOLLIDONE® 25, KOLLIDONE® 30, and KOLLIDONE® VA 64. In addition, the '572 Patent, the '280 Patent, and the '036 Application teach further osmopolymers and osmotic agents (also known as "osmotically effective compounds" or "osmagents") that are suitable for use in the coating suspension of the present invention. The contents of each of the '572 Patent, the '280 Patent, and the '036 Application are incorporated herein in their entirety by reference.

Significantly, it has been found that the coating suspension of the present invention is notably less process sensitive than coating suspensions previously used to provide expandable osmotic layers. In particular, it has been found that the coating suspension of the present invention may be used to coat dosage forms with an expandable osmotic layer under both wet and dry process conditions without running a noticeable risk of creating cracked or defective osmotic layers. The coating suspension of the present invention, therefore, reduces or eliminates the problems associated with the process sensitivity of previously used coating suspensions and thereby facilitates commercial production of controlled release dosage forms incorporating a coated expandable osmotic layer.

Relative to previously coated osmotic layers, the expandable osmotic layer of the present invention is characterized by increased levels of film former and decreased levels of osmopolymer and osmotic agent. In particular, the expandable osmotic layer of the present invention includes between about 25 wt % and about 44 wt % film former, with osmotic layers including about 30 wt % to about 40 wt % film former being preferred and osmotic layers including about 31 wt % to about 39 wt % film former being particularly preferred. As the amount of film former included in the expandable osmotic layer of the present invention varies, the amount of osmopolymer and osmotic agent included in the expandable osmotic layer will also vary. However, the ratio of osmopolymer to osmotic agent included in the expandable osmotic layer of the present invention is maintained at between about 0.5:1 and about 0.7:1, with the expandable osmotic layer being preferably formulated with an osmopolymer to osmotic agent ratio of about 0.6:1. For example, where the expandable osmotic layer of the present invention is coated with a coating suspension formulated to include 5 wt % film former, 4.1 wt % osmopolymer, and 6.9 wt % osmotic agent mixed into a two part solvent mixture including 65.3 wt % water and 18.7 wt % ethanol, the expandable osmotic layer will include about 31.3% film former, about 25.6% osmopolymer, and about 43.1% osmotic agent.

In one embodiment, the expandable osmotic layer of the present invention includes about 31.3 wt % to about 43.8 wt % film former. Exemplary formulations of such an embodiment include the following: an expandable osmotic layer including about 31.3 wt % film former, about 22.9 wt % to about 28.3 wt % osmopolymer, and about 40.4 wt % to about 45.8 wt % osmotic agent; an expandable osmotic layer including about 37.5 wt % film former, about 20.8 wt % to about 25.7 wt % osmopolymer, and about 36.8 wt % to about 41.7 wt % osmotic agent; and an expandable osmotic layer including about 43.8 wt % film former, about 18.7 wt % to about 23.1 wt % osmopolymer, and about 33.1 wt % to about 37.5 wt % osmotic agent.

In another embodiment, the expandable osmotic layer of the present invention is formulated to include about 27.8 wt % to about 41.2 wt % film former. Exemplary formulations of such an embodiment include the following: an expandable osmotic layer including about 27.8 wt % film former, about 24.1 wt % to about 29.7 wt % osmopolymer, and about 42.5 wt % to about 48.1 wt % osmotic agent; an expandable osmotic layer including about 33.3 wt % film former, about 22.2 wt % to about 27.5 wt % osmopolymer, and about 39.2 wt % to about 44.5 wt % osmotic agent; and an expandable osmotic layer including about 41.2 wt % film former, about 19.6 wt % to about 24.2 wt % osmopolymer, and about 34.6 wt % to about 39.2 wt % osmotic agent.

In yet another embodiment, the expandable osmotic layer of the present invention includes about 25 wt % to about 35% wt % film former. Exemplary formulations of such an embodiment of the expandable osmotic layer of the present invention include the following: an expandable osmotic layer that includes about 25 wt % film former, about 25 wt % to about 30.9 wt % osmopolymer, and about 44.1 wt % to about 50 wt % osmotic agent; and expandable osmotic layer that includes about 30 wt % film former, about 23.3 wt % to about 28.8 wt % osmopolymer, and about 41.2 wt % to about 46.7 wt % osmotic agent; and an expandable osmotic layer that includes about 35 wt % film former, about 21.7 wt % to about 26.8 wt % osmopolymer, and about 38.2 wt % to about 43.3 wt % osmotic agent.

The composition of the expandable osmotic layer of the present invention allows the expandable osmotic layer to be coated under varying process conditions, which, in turn, facilitates commercial production of controlled release dosage forms having coated expandable osmotic layers. Surprisingly, despite the increased levels of film former and decreased levels of osmopolymer and osmotic agent included in the expandable osmotic layer of the present invention, the function of the expandable osmotic layer is not compromised relative to expandable osmotic layers previously produced. Therefore, the expandable osmotic layer of the present invention not only facilitates commercial production of controlled release dosage forms having a coated expandable osmotic layer, but the expandable osmotic layer of the present invention does so without compromising the performance of such dosage forms.

Though the expandable osmotic layer of the present invention may be produced by the coating suspension of the present invention using a spray coating process, any suitable composition or process may be used to provide the expandable osmotic layer of the present invention. In one embodiment, the expandable osmotic layer of the present invention includes NATRASOL® as the film former, NaCMC as the osmopolymer, and NaCl as the osmotic agent. Like the coating suspension of the present invention, however, the expandable osmotic layer of the present invention is not limited to NATRASOL® as the film former, NaCMC as the osmopolymer, or NaCl as the osmotic agent. As is easily appreciated, the film formers, osmopolymers, and osmotic agents suitable for use in the coating suspension of the present invention are also suitable for use in the expandable osmotic coating of the present invention.

The dosage form of the present invention is embodied by a controlled release dosage form incorporating the expandable osmotic layer of the present invention. In one embodiment (shown in FIG. 1), the dosage form 10 of the present invention may be a controlled release dosage form including a capsule 12 containing a liquid active agent formulation 14, an expandable osmotic layer 16 according to the present invention coating the capsule 12, a semipermeable layer 18 coating the expandable osmotic layer 16, an exit orifice 20 created through the semipermeable layer 18 and the expandable osmotic layer 16, and, optionally, a barrier layer 22 positioned between the capsule 12 and the expandable osmotic layer 16 according to the present invention. Materials and methods suitable for forming the capsule 12 containing a liquid active agent formulation 14, the optional barrier layer 22, the semipermeable layer 18, and the exit orifice 20 of such a dosage form are taught in the '572 Patent, the '280 Patent, and the '036 Application, the contents of each of which have been incorporated herein by a previous reference.

The expression "active agent" as used herein, encompasses any drug, therapeutic compound, or composition that can be delivered to provide a benefit to the intended subject. The term active agent includes algicide, antioxidant, air purifier, biocide, bactericide, catalyst, chemical reactant, disinfectant, fungicide, fermentation agent, fertility inhibitor, fertility promoter, germicide, plant growth promoter, plant growth inhibitor, preservative, rodenticide, sterilization agent, sex sterilant for insects, and the like. Exemplary active agents that are suitable for delivery from a controlled release capsule and may be incorporated into a liquid active agent formulation are also detailed in '572 Patent, the '280 Patent, and the '036 Application.

As it is used herein, the expression "liquid, active agent formulation" indicates a formulation containing an active agent and is able to flow from a dosage form and into the environment of use. The formulation may be neat liquid active agent, or a solution, suspension, slurry, emulsion, self-emulsifying composition, liposomal solution, or other flowable composition in which the active agent is present. The liquid active agent formulation may be a solid at temperatures lower than the temperature of the environment of use, such as body temperature of humans or animals, but the solid should become a flowable composition after administration of the dosage form of the present invention. A binder, antioxidant, pharmaceutically acceptable carrier, permeation enhancer, or the like may accompany the active agent in the liquid active agent formulation, and the liquid active agent formulation may include a surfactant of mixture of surfactants. The liquid active agent formulation included in a dosage form according to the present invention is formulated such that the liquid active agent does not physically or chemically degrade the device containing the liquid active agent formulation to a degree that compromises the desired performance of the dosage form.

Figure 2:
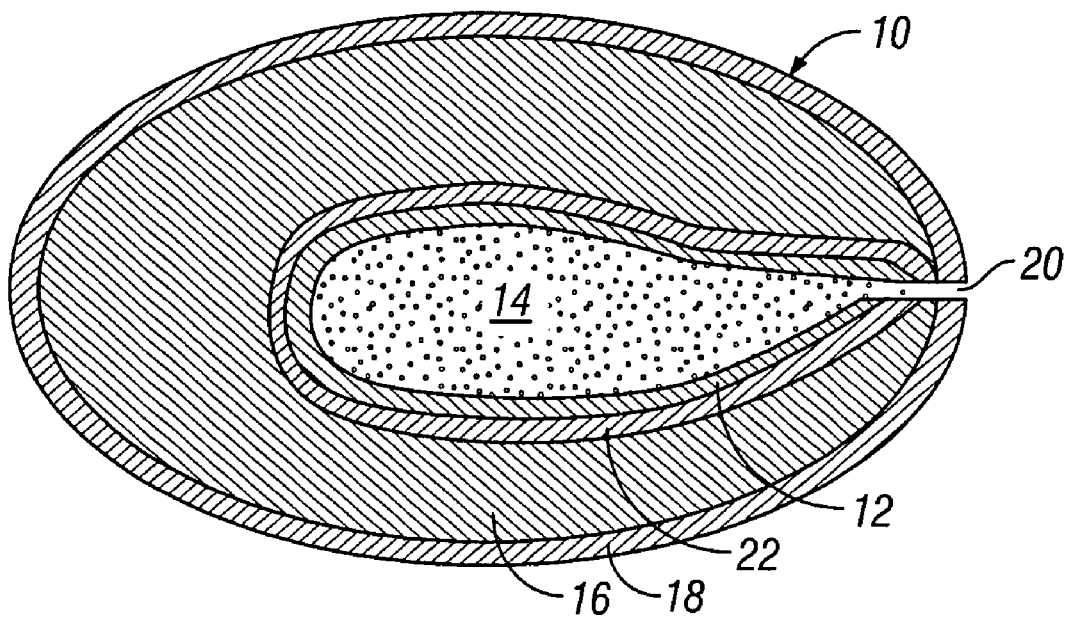
FIG. 2 illustrates the dosage form of FIG. 1 in operation.

FIG. 2 illustrates the dosage form 10 of FIG. 1 in operation. Upon administration of the dosage form 10 to an environment of operation, water from the environment of operation is drawn through the semipermeable layer 18 and into the expandable osmotic layer 16, which causes the expandable osmotic layer 16 to expand, as shown in FIG. 2. As it expands, the expandable osmotic layer 16 exerts a compressive force against the capsule 12 causing the capsule 12 to collapse and expelling the liquid active agent formulation 14 contained within the capsule 12 through the exit orifice 20 and into the environment of operation at a controlled rate over a desired period of time. Advantageously, the release profile provided by the embodiment of the dosage form 10 of the present invention illustrated in FIG. 1 and FIG. 2 can be modified, as desired, by altering one or more aspects of the various components of dosage form 10, such as, for example, by altering the thickness or chemical makeup of the expandable osmotic layer 16 or the semipermeable layer 18 included in the dosage form 10.

Although FIG. 1 and FIG. 2 illustrate a preferred embodiment of the dosage form of the present invention, the dosage form of the present invention is not limited to such a device. The dosage form of the present invention includes any controlled release dosage form utilizing the expandable osmotic layer of the present invention. Typically, where the dosage form of the present invention is designed for human and veterinary pharmaceutical applications, the dosage form of the present invention will be designed to provide delivery of the active agent included in the liquid active agent formulation over a period of time ranging from about 2 hours to about 24 hours, from about 4 hours to about 12 hours, or from about 6 hours to about 8 hours, since dosing may take place from once to several times a day. The dosage form of the present invention can take on a wide variety of shapes, sizes and forms adapted for delivering an active agent to a desired environment of use. For example, the dosage form of the present invention includes buccal, implant, anal, artificial gland, cervical, intrauterine, ear, nose, dermal, vaginal, percutaneous, subcutaneous, and similar delivery systems. Alternatively, the dosage form of the present invention may be designed for packaging or for delivering breath fresheners, perfumes, bath oils containing dermal medicaments, bubble baths containing therapeutics, and the like. Moreover, the dosage form of the present invention can be sized, shaped, structured and adapted for delivering an active agent in streams, aquariums, fields, factories, reservoirs, laboratory facilities, hot houses, transportation means, military means, hospitals, veterinary clinics, nursing homes, farms, zoos, sickrooms, clinics, and other places of use.

The present invention also includes a method of manufacturing a controlled release dosage form. The method of the present invention includes providing an intermediate dosage form. As used in describing the method of the present invention, the term "intermediate dosage form" indicates a device that forms one or more components of a controlled release dosage form of the present invention but is incomplete as a dosage form according to the present invention. The method of the present invention also includes coating the intermediate dosage form with an expandable osmotic layer according to the present invention using a suitable process. In one embodiment, the method of the present invention includes providing a coating suspension according to the present invention and coating the intermediate dosage form with an expandable osmotic layer according to the present invention using a spray coating process. If a spray coating process is used in the method of the present invention, the spray coating process will preferably be a wet spray coating process. Nevertheless, where the method of the present invention includes a spray coating process, a dry spray coating process may also be employed In yet another embodiment, the method of the present invention includes providing an intermediate dosage form having a barrier layer formed thereover, while in an alternative embodiment, the method of the present invention includes providing an intermediate dosage form lacking a barrier layer.

EXAMPLE 1

Various batches of intermediate dosage forms were coated under both wet and dry coating conditions using either a coating suspension according to the present invention or a coating suspension according to a previously used formulation. The coated intermediate dosage forms resulting from such batches were inspected for imperfections to evaluate the process sensitivity of the coating suspensions used. After a first inspection, the dosage forms were coated with a semipermeable layer and the dosage forms were inspected a second time for imperfections. Dosage forms from each batch were chosen for in-vitro release rate testing in order to evaluate the release rate profile achieved by the expandable osmotic layer according to the present invention.

The intermediate dosage forms used in each of the batches were prepared by coating #11 oblong gelatin capsules with a barrier layer. The capsules were each filled with a 200 mg Guaifenesin liquid active agent formulation and were supplied by Banner Pharmacaps®. A barrier layer coating solution for the barrier layer was prepared by mixing 97 wt % Kollicoat SR latex (30% solid) and 3 wt % propylene glycol. The barrier layer coating solution was then sprayed onto the gelatin capsules in a 52" Hi-coater, until a weight gain of about 40 mg per capsule was achieved. Once prepared, the intermediate dosage forms were divided into eight different batches for further processing.

The intermediate dosage forms used in each of the batches were prepared by coating #11 oblong gelatin capsules with a barrier layer. The capsules were each filled with a 200 mg Guaifenesin liquid active agent formulation and were supplied by Banner Pharmacaps®. A barrier layer coating solution for the barrier layer was prepared by mixing 97 wt % KOLLICOAT® SR latex (30% solid) and 3 wt % propylene glycol. The barrier layer coating solution was then sprayed onto the gelatin capsules in a 52" Hi-coater, until a weight gain of about 40 mg per capsule was achieved. Once prepared, the intermediate dosage forms were divided into eight different batches for further processing.

Four different coating suspensions for the application of expandable osmotic layers were prepared. The first coating suspension included 3 wt % NATRASOL®, 4.9 wt % NaCMC (sodium carboxymethylcellulose, 7H4F, MW 700,000), and 8.1 wt % NaCl mixed into 62.7 wt % water and 21.3 wt % ethanol. The second coating suspension included 5 wt % NATRASOL®, 4.1 wt % NaCMC (sodium carboxymethylcellulose, 7H4F, MW 700,000), and 6.9 wt % NaCl mixed into 62.7 wt % water and 21.3 wt % ethanol. The third coating suspension included 3 wt % NATRASOL®4.9 wt % NaCMC (sodium carboxymethylcellulose, 7H4F, MW 700,000), and 8.1 wt % NaCl mixed into 65.3 wt % water and 18.7 wt % ethanol. And the fourth coating suspension included 5 wt % NATRASOL®, 4.1 wt % NaCMC (sodium carboxymethylcellulose, 7H4F, MW 700,000), and 6.9 wt % NaCl mixed into 65.3 wt % water and 18.7 wt % ethanol. To prepare each of the coating suspensions, the NATRASOL® and NaCMC included in each suspension were suspended in the appropriate amount of ethanol in a first container, and, in a second container, the amount of NaCl included in each coating suspension was dissolved in the appropriate amount of water. The coating suspensions were then completed by slowly adding the NaCl solution used in each suspension to the corresponding ethanol suspension with constant mixing.

Table 2 details the coating suspension used in each coating run, the coating conditions of each coating run, the coating efficiency achieved by each coating run, and the percentage of cracked devices (coated intermediate dosage forms) resulting from each coating run. As is easily appreciated by reference to Table 2, coating runs 24_14 and 24_18, which were conducted under wet process conditions and utilized coating suspensions according to the present invention, did not produce any cracked devices. In contrast, coating runs 24_13 and 24_17, which were also conducted under wet process conditions but utilized coating suspensions according to a previously used formulation, produced a measurable percentage of cracked devices, with 0.19% of the devices produced in the 24_13 coating run exhibiting cracks and 0.14% of the devices produced in the 24_17 coating run exhibiting cracks. None of the four coating suspensions produced devices having cracked expandable osmotic layers when the coating runs were monitored to ensure dry coating processes. As is easily appreciated from the results provided in Table 2, the coating formulations of the present invention did not exhibit the process sensitivity that characterizes the previously used coating formulations.

After each batch of coated intermediate dosage forms was inspected, the devices were then coated with a semipermeable layer. The coating solution used to coat each batch with a semipermeable layer was prepared by dissolving cellulose acetate (CA398-10) and Pluronic F108 at a ratio of about 4:1 (w/w) in acetone such that a final coating solution containing 4% (w/v) solids was provided. The coating solution was then applied to each batch of devices in a 24" Hi-coater at a rate of about 180 g/min, with the final weight gain of semipermeable layer being about 125 mg per device. After coating each batch with a semipermeable layer, the devices, now coated with an expandable osmotic layer and a semipermeable layer, were inspected a second time.

After each batch of coated intermediate dosage forms was inspected, the devices were then coated with a semipermeable layer. The coating solution used to coat each batch with a semipermeable layer was prepared by dissolving cellulose acetate (CA398-10) and PLURONIC® F108 (2-methyloxirane) at a ratio of about 4:1 (w/w) in acetone such that a final coating solution containing 4% (w/v) solids was provided. The coating solution was then applied to each batch of devices in a 24" Hi-coater at a rate of about 180 g/min, with the final weight gain of semipermeable layer being about 125 mg per device. After coating each batch with a semipermeable layer, the devices, now coated with an expandable osmotic layer and a semipermeable layer, were inspected a second time.

EXAMPLE 2

To compare the function of an expandable osmotic layer according to the present invention to the function of a previously used expandable osmotic layer, devices from each of the batches processed in Example 1 were tested in-vitro. Devices without cracks were selected from each of the eight batches and were provided with an exit orifice. The exit orifice of each of device was formed using a programmable micro drill and was about 40 mil in diameter and 30 mil in depth. Once provided with an exit orifice, the devices were introduced into 900 ml of AIF and the release rate profile was determined using a USP II paddle method at 100-rpm agitation speed. The Guaifenesin concentration in the release medium was assayed with a UV spectrophotometer at a wavelength of 276 nm.

Figure 3:
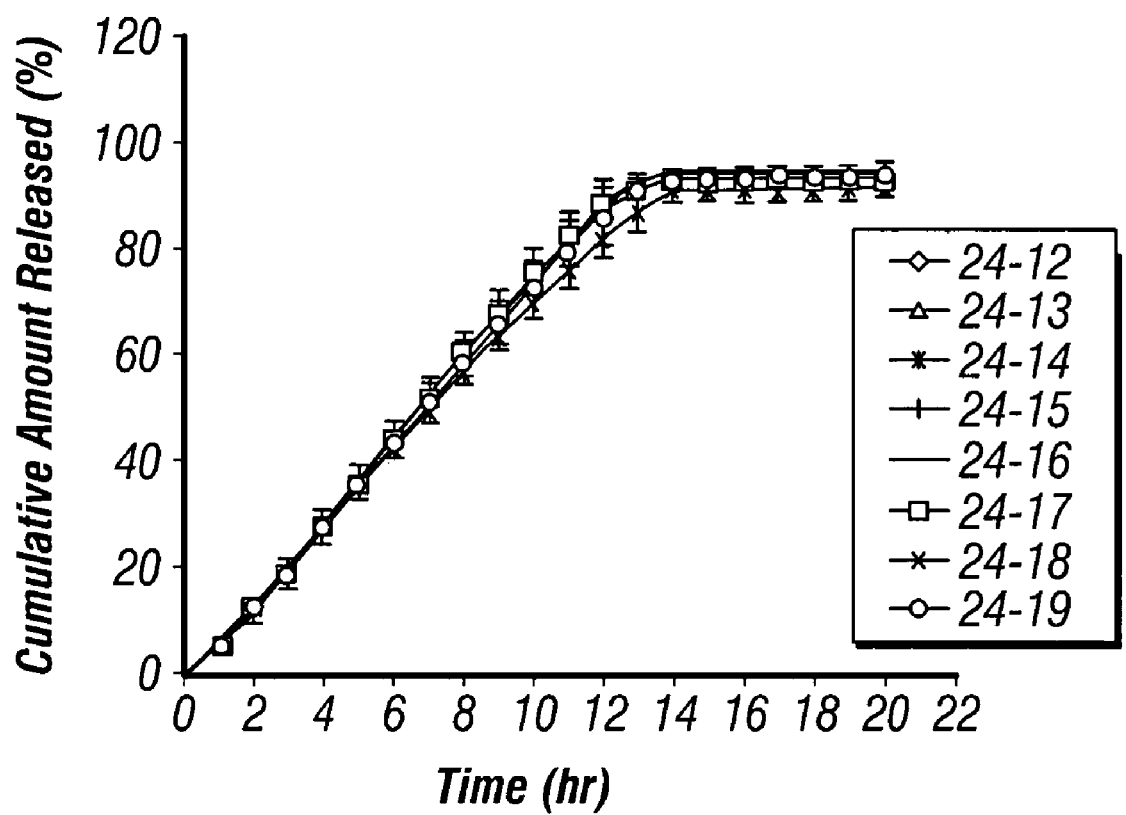
FIG. 3 provides a graph illustrating the in-vitro release profile of various controlled release liquid capsules.

FIG. 3 provides a graph illustrating allowing a comparison of the release rate profiles provided by the devices produced in each of the eight batches described in Example 1. As can be appreciated by reference to FIG. 3, the devices generated in coating runs 24_14, 24_15, 24_18 and 24_19 provided substantially the same controlled release performance as the devices generated in coating runs 24_12, 24_13, 24_16, and 24_17.

We claim:

1. A coating suspension for an expandable osmotic layer of a dosage form consisting essentially of:
    sodium carboxymethylcellulose as an osmopolymer;
    sodium chloride as an osmotic agent;
    hydroxyethylcellulose as a film former, wherein the coating suspension includes from about 5 wt % to about 7 wt % of the film former; and
    a two part solvent system;
    wherein the ratio of osmopolymer to osmotic agent included in the coating suspension is about 0.5:1 to about 0.7:1.

2. The coating suspension of claim 1, wherein the total solids content of the coating suspension is from about 16 wt % to about 20 wt %.

3. The coating suspension of claim 1, wherein the total solids content of the coating suspension is from about 16 wt % to about 18 wt %.

4. The coating suspension of claim 1, wherein the total solids content of the coating suspension is about 16 wt %.

5. The coating suspension of claim 1, wherein the total solids content of the coating suspension is about 18 wt %.

6. The coating suspension of claim 1, wherein the total solids content of the coating suspension is about 20 wt %.

7. The coating suspension of claim 1, wherein the ratio of osmopolymer to osmotic agent included in the coating suspension is about 0.6:1.

8. The coating suspension of claim 1, wherein the coating suspension includes about 5 wt % film former.

9. The coating suspension of claim 1, wherein the coating suspension includes about 6 wt % film former.

10. The coating suspension of claim 1, wherein the coating suspension includes about 7 wt % film former.

11. The coating suspension of claim 1, wherein the two part solvent system accounts for about 80 wt % to about 84 wt % of the coating suspension.

12. The coating suspension of claim 1, wherein the two part solvent system accounts for about 80 wt % to about 82 wt % of the coating suspension.

13. The coating suspension of claim 1, wherein the two part solvent system accounts for about 80 wt % of the coating suspension.

14. The coating suspension of claim 1, wherein the two part solvent system accounts for about 82 wt % of the coating suspension.

15. The coating suspension of claim 1, wherein the two part solvent system accounts for about 84 wt % of the coating suspension.

16. The coating suspension of claim 1, wherein the osmopolymer, the osmotic agent, and the film former account for about 16 wt % to about 20 wt % of the coating suspension, with the coating suspension including about 5 wt % to about 7 wt % film former, about 3 wt % to about 6.2 wt % osmopolymer, and about 5.3% to about 10% osmotic agent.

17. The coating suspension of claim 16, wherein the two part solvent system accounts for about 80 wt % to about 84 wt % of the coating suspension.

18. The coating suspension of claim 17, wherein the two part solvent system includes an organic solvent and an aqueous solvent, wherein the organic solvent is miscible with the aqueous solvent and the osmopolymer is poorly soluble in the organic solvent.

19. The coating suspension of claim 17, wherein the two part solvent system comprises ethanol and water.

20. The coating suspension of claim 19, wherein the ratio of ethanol to water included in the two part solvent system is about 1:2 to about 1:4.

21. The coating suspension of claim 19, wherein the ratio of ethanol to water included in the two part solvent system is about 1:2.2 to about 1:3.5.

22. The coating suspension of claim 19, wherein the wherein the osmopolymer, the osmotic agent, and the film former account for about 16 wt % of the coating suspension, and the ratio of ethanol to water included in the two part solvent system is about 1:3 to about 1:3.5.

23. The coating suspension of claim 19, wherein the wherein the osmopolymer, the osmotic agent, and the film former account for about 20 wt % of the coating suspension, and the ratio of ethanol to water included in the two part solvent system is about 1:2 to about 1:2.2.

24. The coating suspension of claim 17, wherein the osmopolymer, the osmotic agent, and the film former account for about 16 wt % the coating suspension, with the coating suspension including about 5 wt % film former, about 3.7 wt % to about 4.5 wt % osmopolymer, and about 6.5 wt % to about 7.3 wt % osmotic agent.

25. The coating suspension of claim 17, wherein the osmopolymer, the osmotic agent, and the film former account for about 16 wt % the coating suspension, with the coating suspension including about 5 wt % film former, about 4.1 wt % osmopolymer, and about 6.9 wt % osmotic agent.

26. The coating suspension of claim 17, wherein the osmopolymer, the osmotic agent, and the film former account for about 16 wt % the coating suspension, with the coating suspension including about 6 wt % film former, about 3.3 wt % to about 4.1 wt % osmopolymer, and about 5.9 wt % to about 6.7 wt % osmotic agent.

27. The coating suspension of claim 17, wherein the osmopolymer, the osmotic agent, and the film former account for about 16 wt % the coating suspension, with the coating suspension including about 6 wt % film former, about 3.7 wt % osmopolymer, and about 6.3 wt % osmotic agent.

28. The coating suspension of claim 17, wherein the osmopolymer, the osmotic agent, and the film former account for about 16 wt % the coating suspension, with the coating suspension including about 7 wt % film former, about 3 wt % to about 3.7 wt % osmopolymer, and about 5.3 wt % to about 6 wt % osmotic agent.

29. The coating suspension of claim 17, wherein the osmopolymer, the osmotic agent, and the film former account for about 16 wt % the coating suspension, with the coating suspension including about 7 wt % film former, about 3.4 wt % osmopolymer, and about 5.6 wt % osmotic agent.

30. The coating suspension of claim 17, wherein the osmopolymer, the osmotic agent, and the film former account for about 18 wt % the coating suspension, with the coating suspension including about 5 wt % film former, about 4.3 wt % to about 5.4 wt % osmopolymer, and about 7.6 wt % to about 8.7 wt % osmotic agent.

31. The coating suspension of claim 17, wherein the osmopolymer, the osmotic agent, and the film former account for about 18 wt % the coating suspension, with the coating suspension including about 5 wt % film former, about 4.9 wt % osmopolymer, and about 8.1 wt % osmotic agent.

32. The coating suspension of claim 17, wherein the osmopolymer, the osmotic agent, and the film former account for about 18 wt % the coating suspension, with the coating suspension including about 6 wt % film former, about 4 wt % to about 4.9 wt % osmopolymer, and about 7.1 wt % to about 8 wt % osmotic agent.

33. The coating suspension of claim 17, wherein the osmopolymer, the osmotic agent, and the film former account for about 18 wt % the coating suspension, with the coating suspension including about 6 wt % film former, about 4.5 wt % osmopolymer, and about 7.5 wt % osmotic agent.

34. The coating suspension of claim 17, wherein the osmopolymer, the osmotic agent, and the film former account for about 18 wt % the coating suspension, with the coating suspension including about 7 wt % film former, about 3.7 wt % to about 4.5 wt % osmopolymer, and about 6.5 wt % to about 7.3 wt % osmotic agent.

35. The coating suspension of claim 17, wherein the osmopolymer, the osmotic agent, and the film former account for about 18 wt % the coating suspension, with the coating suspension including about 7 wt % film former, about 4.1 wt % osmopolymer, and about 6.9 wt % osmotic agent.

36. The coating suspension of claim 17, wherein the osmopolymer, the osmotic agent, and the film former account for about 20 wt % the coating suspension, with the coating suspension including about 5 wt % film former, about 5 wt % to about 6.2 wt % osmopolymer, and about 8.8 wt % to about 10 wt % osmotic agent.

37. The coating suspension of claim 17, wherein the osmopolymer, the osmotic agent, and the film former account for about 20 wt % the coating suspension, with the coating suspension including about 5 wt % film former, about 5.6 wt % osmopolymer, and about 9.4 wt % osmotic agent.

38. The coating suspension of claim 17, wherein the osmopolymer, the osmotic agent, and the film former account for about 20 wt % the coating suspension, with the coating suspension including about 6 wt % film former, about 4.7 wt % to about 5.8 wt % osmopolymer, and about 8.2 wt % to about 9.3 wt % osmotic agent.

39. The coating suspension of claim 17, wherein the osmopolymer, the osmotic agent, and the film former account for about 20 wt % the coating suspension, with the coating suspension including about 6 wt % film former, about 5.3 wt % osmopolymer, and about 8.7 wt % osmotic agent.

40. The coating suspension of claim 17, wherein the osmopolymer, the osmotic agent, and the film former account for about 20 wt % the coating suspension, with the coating suspension including about 7 wt % film former, about 4.3 wt % to about 5.4 wt % osmopolymer, and about 7.6 wt % to about 8.7 wt % osmotic agent.

41. The coating suspension of claim 17, wherein the osmopolymer, the osmotic agent, and the film former account for about 20 wt % the coating suspension, with the coating suspension including about 7 wt % film former, about 4.9 wt % osmopolymer, and about 8.1 wt % osmotic agent.

42. A method for making a dosage form, the method comprising:
   providing an intermediate dosage form;
   providing a coating suspension consisting essentially of sodium carboxymethylcellulose as an osmopolymer, sodium chloride as an osmotic agent, hydroxyethylcellulose as a film former, wherein the coating suspension includes from about 5 wt % to about 7 wt % of the film former, and a two part solvent system, wherein the ratio of osmopolymer to osmotic agent included in the coating suspension is about 0.5:1 to about 0.7:1;
   coating the intermediate dosage form with the coating suspension.

43. The method according to claim 42, wherein said coating of the intermediate dosage form with the coating suspension is carried out under wet process conditions.

44. The method according to claim 42, wherein said coating of the intermediate dosage form is carried out under process conditions that result in a coating efficiency of about 80% or less.

* * * * *